US005443953A

United States Patent [19]
Hansen et al.

[11] Patent Number: 5,443,953
[45] Date of Patent: Aug. 22, 1995

[54] PREPARATION AND USE OF IMMUNOCONJUGATES

[75] Inventors: Hans J. Hansen, Mystic Island; Shui-on Leung, Madison; Jerry Shevitz, Livingston, all of N.J.

[73] Assignee: Immunomedics, Inc., Morris Plains, N.J.

[21] Appl. No.: 162,912

[22] Filed: Dec. 8, 1993

[51] Int. Cl.$^6$ ..................... A61K 39/395; C07K 16/00
[52] U.S. Cl. ................... 424/1.49; 424/1.53; 424/178.1; 424/179.1; 424/180.1; 424/181.1; 424/182.1; 424/183.1; 424/9.341; 435/7.2; 435/7.23; 435/69.6; 435/172.1; 435/7.1; 530/387.3; 530/391.3; 530/391.5; 530/391.7; 530/391.9
[58] Field of Search ...................... 435/7.2, 7.23, 69.6, 435/172.1, 7.1; 530/391.3, 391.5, 391.7, 391.9, 387.3; 424/85.8, 85.91, 178.1, 183.1, 1.49, 1.53, 9

[56] References Cited

U.S. PATENT DOCUMENTS 4,867,973 9/1989 Goers et al. .................. 424/85.91
5,057,313 10/1991 Shih et al. .................... 424/85.91

FOREIGN PATENT DOCUMENTS 9010700 9/1990 WIPO .

OTHER PUBLICATIONS

Brown, "Clinical Use Of Monoclonal Antibodies", *Clinical Use Of Monoclonal Antibodies*, pp. 227–250.
Goldenberg et al., "Targeting, Dosimetry, and Radioimmunotherapy of B-Cell Lymphomas With Iodine-131-Labeled LL2 Monoclonal Antibody", *Journal of Clinical Oncology*, vol. 9:548–564, (1991).
Kanellos et al., "Studies Of Methotrexate-Monoclonal Antibody Conjugates For Immunotherapy", *JncI.*, vol. 75:319–329, (1985).
Kreitman et al., "Cytotoxicity of Conjugates Between LL.2 And Derivatives Of Pseudomonas Exotoxin Toward B-Cell Non-Hodgkin's Lymphoma", *Immunology*, vol. 33–344, (1992).
Kulkarni et al., "Covalent Binding Of Methotrexate To Immunoglobulins And The Effect Of Antibody-Linked Drug On Tumor Growth in Vivo", *Cancer Research*, vol. 41:2700–2706, (1981).
Murthy et al., "Lymphoma Imaging With A New Technetium-99m Labelled Antibody, LL2", *Nuclear Medicine*, pp. 394–401, (1992).
Orlandi et al., "Cloning Immunoglubulin Variable Domains For Expression By The Polymerase Chain Reaction", *Proc. Natl. Acad. Sci. USA*, vol. 86:3833–3837, (1989).
Pawlak-Byczkowska et al., "Tow New Monoclonal Antibodies, EPB-1 and EPB-2 Reactive With Human Lymphoma", *Cancer*, vol. 49:4568–4577, (1989).
Shih et al., "Site-Specific Linkage Of Methotrexate To Monoclonal Antibodies Using An Intermediate Carrier", *Int. J. Cancer*, vol. 41:832–839, (1988).

(List continued on next page.)

Primary Examiner—David Saunders
Attorney, Agent, or Firm—Foley & Lardner

[57] ABSTRACT

The present invention relates to immunoconjugates comprising an antibody fragment which is covalently bound to a diagnostic or therapeutic principle through a carbohydrate moiety in the light chain variable region of the antibody fragment. The invention also relates to immunoconjugates comprising an antibody moiety that is an intact antibody containing a glycosylation site in the light chain variable domain which has been introduced into the antibody by mutating the nucleotide sequence encoding the light chain. The resultant immunoconjugates retain the immunoreactivity of the antibody fragment or intact antibody, and target the diagnostic or therapeutic principle to a target tissue where the diagnostic or therapeutic effect is realized. Thus, the invention contemplates the use of such immunoconjugates for diagnosis and immunotherapy. The invention further relates to methods for preparing such immunoconjugates.

17 Claims, No Drawings

OTHER PUBLICATIONS

Shih et al., "A Fluorouridine-Anti-CEA Immunoconjugate Is Therapeutically Effective In A Human Colonic Cancer Xenograft Model", *Int. J. Cancer,* vol. 46:1101–1106, (1990).

Shih et al., "Anthracycline Immunoconjugates Prepared By A Site-Specific Linkage Via An Amino-Dextran Intermediate Carrier", *Cancer Research,* vol. 51:4192–4198, (1991).

Co et al., "Chimeric And Humanized Antibodies With Specificity For The CD33 Antigen", *The Journal Of Immunology,* vol. 148:1149–1154, (1992).

Vaughn et al., "Limiting To The Killing Of Tumours Using Radiolabelled Antibodies", *The British Journal Of Radiology,* vol. 60:567–578, (1987).

Wallick et al., "Glycosylation Of A $V_H$ Residue Of A Monoclonal Antibody Against $\alpha(1\rightarrow6)$ Dextran Increases Its Affinity For Antigen", *J. Exp. Med.,* vol. 168:1099–1109, (1988).

Wright et al., "Antibody Variable Region glycosylation: Position Effects On Antigen Binding And Carbohydrate Structure", *The EMBO Journal,* vol. 10:2717–2723, (1991).

J. R. Couto et al, *Hybridoma,* 12, 485–489, 1993.

PREPARATION AND USE OF IMMUNOCONJUGATES

BACKGROUND OF THE INVENTION

1. Field of the Invention

This invention is directed to novel immunoconjugates that are useful for diagnosis and therapy. In particular, this invention is directed to immunoconjugates comprising an antibody fragment which is covalently bound to a diagnostic or therapeutic principle through a carbohydrate moiety in the light chain variable region of the antibody fragment. This invention is also directed to immunoconjugates comprising an antibody moiety that is an intact antibody containing a glycosylation site in the light chain variable domain which has been introduced into the antibody by mutating the nucleotide sequence encoding the light chain. This invention is further directed to methods for preparing such immunoconjugates. This invention also is directed to methods of diagnosis and therapy using such immunoconjugates.

2. Related Art

Monoclonal antibodies can be conjugated to a variety of agents to form immunoconjugates for use in diagnosis and therapy. These agents include chelates, which allow the immunoconjugate to form a stable bond with radioisotopes, and cytotoxic agents such as toxins and chemotherapy drugs. For example, cytotoxic agents that normally would be too toxic to patients when administered in a systemic fashion can be coupled to anticancer antibodies in such a manner that their toxic effects become directed only to the tumor cells bearing the target antigens. The diagnostic or therapeutic efficacy of immunoconjugates depends upon several factors. Among these factors, the molar ratio of the diagnostic or therapeutic principle to antibody and the antibody binding activity of the immunoconjugate are of major concern.

Researchers have found that the maximum number of diagnostic or therapeutic principles that can be directly linked to an antibody is limited by the number of modifiable sites on the antibody molecule and the loss of immunoreactivity of the antibody. For example, Kulkarni et al., *Cancer Research* 41:2700–2706 (1981), have reported that there is a limit to the number of drug molecules that can be incorporated into an antibody without significantly decreasing antigen-binding activity. Kulkarni et al., found that the highest incorporation obtained for methotrexate was about ten methotrexate molecules per-molecule of antibody, and that attempts to increase the drug-antibody molar ratio over about ten decreased the yield of immunoconjugate and damaged antibody activity. Kanellos et al., *JNCI* 75:319–329 (1985), have reported similar results.

In order to achieve a high substitution level of drug-immunoconjugate without significantly impairing antigen-binding activity, researchers have investigated the use of a water-soluble polymeric molecule as an intermediary for the indirect conjugation of the drug. Such polymers include oxidized dextran (Arnon et al., *Immunol. Rev.* 62:5–27 (1982)), poly-glutamic acid (Greenfield et al., *Antibody Immunoconjugates and Radiopharmaceuticals* 2:201–216 (1989)), human serum albumin (Baldwin et al., *NCI Monographs* 3:95–99 (1987)), and carboxymethyldextran (Schechter et al., *Cancer Immunol. Immunother.* 25:225–230 (1987)).

Shih et al., *Int. J. Cancer* 41:832–839 (1988), have described a site-specific linking method in which methotrexate was linked to the carbohydrate moiety in the constant, or "Fc," region of an antibody via amino-dextran, resulting in an immunoconjugate with high substitution ratio and retention of immunoreactivity. More recently, Shih et al., *Int. J. Cancer* 46:1101–1106 (1990), demonstrated the efficacy of an immunoconjugate comprising 5-fluorouridine conjugated via amino-dextran to the carbohydrate moiety in the Fc region of a monoclonal antibody. In both studies, Shih et al. found that the immunoconjugate contained approximately 30–50 molecules of drug per molecule of immunoglobulin. Thus, indirect conjugation of a diagnostic or therapeutic principle to a carbohydrate moiety in the Fc region of an antibody provides a means to obtain immunoconjugates with functional antigen binding activity and a high substitution level.

An advantage of using the carbohydrate moiety in the Fc region as a site-specific attachment site is that antibodies of all subtypes typically contain a glycosylated Fc region. In general, antibody molecules are glycosylated in their Fc regions at characteristic positions according to their isotype. For example, carbohydrate is typically present at amino acid 297 in the $C_H2$ domain in the Fc region of IgG molecules. Conjugating a diagnostic or therapeutic principle to the carbohydrate group at this position, which is far away from the antigen binding site, should produce a minimal effect on the immunoreactivity of the resultant immunoconjugate, as demonstrated by Shih et al.

However, a disadvantage of using the carbohydrate moiety in the Fc region as an attachment site is that the entire antibody is required for the immunoconjugate. The use of antibody fragments, particularly Fab, Fab' and F(ab')₂ provide an advantage over the use of an entire antibody because such fragments are better able to diffuse out of capillaries and into target tissues. For example, see Brown, "Clinical Use of Monoclonal Antibodies," in BIOTECHNOLOGY AND PHARMACY, Pezzuto et al., eds. Chapman and Hall, pp.227–249 (1993). Moreover, antibody fragments will clear from blood and normal tissues more readily than an entire antibody. For example, intact murine IgG has a blood half-life of approximately 30 hours, while F(ab')₂ and Fab/Fab' have half-lives of approximately 20 hours and 2 hours, respectively. Id. Thus, it is advantageous to use antibody fragments for constructing immunoconjugates. Antibody fragments are particularly advantageous in radioimmunotherapy and radioimmunodiagnosis applications in which the exposure of normal tissues to radioisotopes must be minimized.

Antibody variable regions occasionally contain carbohydrate groups which provide potential attachment sites for the preparation of immunoconjugates from antibody fragments. For example, asparagine-linked carbohydrate acceptor sequences have been identified in approximately 15–25% of murine variable regions. Kabat et al. SEQUENCES OF PROTEINS OF IMMUNOLOGICAL INTEREST, 5th ed. U.S. Department of Health and Human Services (1990). In the case of the anti-dextran family of antibodies, glycosylation sites reside in the complementarity-determining regions (CDRs), particularly CDR2, of the heavy chain variable regions. Id. The presence of Asn-linked carbohydrates in the CDRs of these antibodies appeared to enhance antigen binding. Wallick et al., *J. Exp. Med.* 168:1099–1109 (1988); Wright et al., *EMBO J.*

10:2717–2723 (1991). However, introduction of additional carbohydrate attachment sites in CDR2 by site-directed mutagenesis resulted in either the enhancement or reduction of affinity for antigen, depending on the position where the glycosylation site was introduced. Wright et al., supra. Thus, the feasibility of attaching a diagnostic or therapeutic principle to a carbohydrate moiety in the VH CDR region is uncertain.

Studies by the present inventors on carbohydrate conjugation demonstrated a high conjugation efficiency with the IgG antibody, LL2, which is a murine monoclonal antibody described by Pawlak-Byczkowska et al. (*Cancer Res.* 49:4568–4577 (1989)) and Goldenberg et al. (*J. Clin. Oncol.* 9:548 (1991)). Analysis of LL2 conjugates using sodium dodecyl-sulfate polyacrylamide gel electrophoresis (SDS-PAGE) under reducing conditions indicated the existence of a glycosylation site in the light chain variable (VL) region of the LL2 antibody. After cloning the VL region of LL2, an Asn-linked glycosylation site at position 18–20 of the framework-1 (FR1) sequence of the VL region was found.

These studies suggested a possible preferential conjugation at a carbohydrate moiety within the VL region. This unexpected finding may be explained by an improved accessibility in the VL region. We used site-directed mutagenesis to remove the Asn-linked glycosylation site and found that the resulting protein exhibited similar immunoreactivity compared with the original antibody. This result is in agreement with the inventors' computer modeling studies which suggested negligible or minimal interaction between the light chain FR1 carbohydrate moiety and the antigen binding site. Thus, these studies indicate that conjugation of a diagnostic or therapeutic principle to a carbohydrate moiety in the FR1 sequence of the VL region provides a means to obtain immunoconjugates of antibody fragments with functional antigen binding activity.

The present invention provides a method for preparing novel immunoconjugates comprising a diagnostic or therapeutic principle which is attached to an intact antibody, or antigen-binding fragment thereof, via a carbohydrate moiety of the light chain variable region.

SUMMARY OF THE INVENTION

The present invention is directed to a soluble immunoconjugate, comprising:
(a) a fragment of an intact antibody, wherein the antibody fragment is selected from the group consisting of-Fab, Fab', F(ab)2, and F(ab')2, and wherein the antibody fragment comprises a light chain variable region and a carbohydrate moiety attached at about amino acid position 18 of the light chain variable region; and
(b) an intermediate conjugate, comprising a polymer carrier having at least one free amine group and a plurality of drug, toxin, chelator, boron addend or detectable label molecules covalently bound to the polymer carrier, wherein the intermediate conjugate is covalently bound through at least one free amine group of the polymer carrier to the carbohydrate moiety of the antibody fragment, and wherein the immunoconjugate retains the immunoreactivity of the antibody fragment.

In addition, the present invention is directed to a soluble immunoconjugate, comprising:
(a) a fragment of an intact antibody, wherein the antibody fragment is selected from the group consisting of Fab, Fab', F(ab)2, and F(ab')2, and wherein the antibody fragment comprises a light chain variable region and a carbohydrate moiety attached at about amino acid position 18 of the light chain variable region; and
(b) a non-antibody moiety selected from the group consisting of a drug, a toxin, a chelator, a boron addend and a detectable label molecule, wherein the non-antibody moiety is covalently bound to the carbohydrate moiety of the antibody fragment, and wherein the immunoconjugate retains the immunoreactivity of the antibody fragment.

The present invention is further directed to a soluble immunoconjugate, comprising:
(a) a mutated antibody, wherein the mutated antibody comprises a light chain variable region and a carbohydrate moiety attached at about amino acid position 18 of the light chain variable region; and
(b) a non-antibody moiety selected from the group consisting of a drug, a toxin, a chelator, a boron addend and a detectable label molecule,
wherein the non-antibody moiety is covalently bound to the carbohydrate moiety of the mutated antibody,
and wherein the immunoconjugate retains the immunoreactivity of the mutated antibody.

The present invention is also directed to a soluble immunoconjugate, comprising:
(a) an antibody component, wherein the antibody component is selected from the group consisting of an Fv and a single chain antibody, and wherein the antibody component comprises a light chain variable region and a carbohydrate moiety attached at about amino acid position 18 of the light chain variable region; and
(b) an intermediate conjugate, comprising a polymer carrier having at least one free amine group and a plurality of drug, toxin, chelator, boron addend or detectable label molecules covalently bound to the polymer carrier,
wherein the intermediate conjugate is covalently bound through at least one free amine group of the polymer carrier to the carbohydrate moiety of the antibody component,
and wherein the immunoconjugate retains the immunoreactivity of the antibody component.

The present invention is further directed to a soluble immunoconjugate, comprising:
(a) an antibody component, wherein the antibody component is selected from the group consisting of an Fv and a single chain antibody, and wherein the antibody component comprises a light chain variable region and a carbohydrate moiety attached at about amino acid position 18 of the light chain variable region; and
(b) a non-antibody component selected from the group consisting of a drug, a toxin, a chelator, a boron addend and a detectable label molecule,
wherein the non-antibody component is covalently bound to the carbohydrate moiety of the antibody component,
and wherein the immunoconjugate retains the immunoreactivity of the antibody component.

The present invention is also directed to a method for preparing an immunoconjugate, comprising the steps of:
(a) introducing an Asn-glycosylation site at about position 18 of the light chain of an antibody by mutating the nucleotide sequence of a DNA molecule encoding the light chain;

(b) cloning the mutated DNA molecule into an expression vector;

(c) transforming host cells with the expression vector, and recovering transformed host cells which express a mutated antibody comprising a mutated light chain and a heavy chain;

(d) culturing the transformed host cells and recovering the mutated antibody from the cultured host cells;

(e) preparing an antibody fragment from the recovered antibody, wherein the antibody fragment is selected from the group consisting of Fab, Fab', F(ab)$_2$, and F(ab')$_2$, and wherein the antibody fragment contains a carbohydrate moiety in the mutated light chain of the antibody fragment; and (f) covalently binding an intermediate conjugate to the carbohydrate moiety of the antibody fragment, wherein the intermediate conjugate comprises a polymer carrier having at least one free amine group and a plurality of drug, toxin, chelator, boron addend or detectable label molecules covalently bound to the polymer carrier, wherein the intermediate conjugate is covalently bound through at least one free amine group of the polymer carrier to the carbohydrate moiety of the antibody fragment, and wherein the immunoconjugate retains the immunoreactivity of the antibody fragment.

The present invention is also directed to a method for diagnosing the presence of a disease in a mammal, comprising the steps of:

(a) preparing an immunoconjugate comprising a detectable label and an antibody fragment having a carbohydrate moiety attached at about position 18 of the light chain of the antibody fragment, wherein the detectable label is conjugated to the carbohydrate moiety of the antibody fragment, and wherein the antibody fragment is capable of binding to an antigen which is associated with the disease;

(b) administering a composition comprising the immunoconjugate and a pharmaceutically acceptable carrier to the mammal; and (c) using in vivo imaging to detect the presence of the immunoconjugate at disease sites.

The present invention is further directed to a method for treating a disease in a mammal, comprising the steps of:

(a) preparing an immunoconjugate comprising an antibody fragment having a carbohydrate moiety attached at about position 18 of the light chain of the antibody fragment and a non-antibody moiety selected from the group consisting of a drug, a toxin, a chelator, a boron addend and a radioisotope, wherein the non-antibody moiety is covalently bound to the carbohydrate moiety of the antibody fragment, and wherein the antibody fragment is capable of binding to an antigen which is associated with the disease; and (b) administering a composition comprising the immunoconjugate and a pharmaceutically acceptable carrier to the mammal.

Also included in the present invention are improved methods of in vitro immunoassay and in situ detection of antigen in histological specimens using the immunoconjugates of the invention.

DETAILED DESCRIPTION

1. Overview

This invention is directed to immunoconjugates comprising an intact antibody, or antigen-binding fragment thereof, which is covalently bound to a diagnostic or therapeutic principle through a carbohydrate moiety in the light chain variable region of the antibody moiety. This invention further relates to methods for preparing such immunoconjugates. The invention also contemplates the use of such immunoconjugates for diagnosis and immunotherapy.

2. Definitions

In the description that follows, a number of terms are utilized extensively. Definitions are herein provided to facilitate understanding of the invention.

Antibody. As used herein, "antibody" includes monoclonal antibodies, such as murine, chimeric, or humanized antibodies, as well as antigen-binding fragments thereof Such fragments include Fab, Fab', F(ab)$_2$, and F(ab')$_2$, which lack the Fc fragment of an intact antibody. Such fragments also include isolated fragments consisting of the light chain variable region, "Fv" fragments consisting of the variable regions of the heavy and light chains, and recombinant single chain polypeptide molecules in which light and heavy variable regions are connected by a peptide linker.

Mutated Antibody. As used herein, a mutated antibody is an intact antibody, or antigen-binding fragment thereof, having an Asn-linked glycosylation site at about amino acid position 18 in the light chain, which has been introduced into the light chain by altering the corresponding nucleotide sequence. Methods of mutating the nucleotide sequence encoding a light chain include the polymerase chain reaction, site-directed mutagenesis, and gene synthesis using the polymerase chain reaction with synthetic DNA oligomers.

Diagnostic or Therapeutic Principle. As used herein, a diagnostic or therapeutic principle is a molecule or atom which is conjugated to an antibody to produce an immunoconjugate which is useful for diagnosis and for therapy. Examples of diagnostic or therapeutic principles include drugs, toxins, chelators, boron compounds, and detectable labels.

Immunoconjugate. As used herein, an immunoconjugate is a molecule comprising an antibody and a diagnostic or therapeutic principle. An immunoconjugate retains the immunoreactivity of the antibody, i.e., the antibody moiety has roughly the same, or only slightly reduced, ability to bind the antigen after conjugation as before conjugation.

Structural gene. A DNA sequence that is transcribed into messenger RNA (mRNA) which is then translated into a sequence of amino acids characteristic of a specific polypeptide.

Promoter. A DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

Enhancer. A promoter element. An enhancer can increase the efficiency with which a particular gene is transcribed into mRNA irrespective of the distance or orientation of the enhancer relative to the start site of transcription.

Complementary DNA (cDNA). Complementary DNA is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complement.

Expression. Expression is the process by which a polypeptide is produced from a structural gene. The process involves transcription of the gene into mRNA and the translation of such mRNA into polypeptide(s).

Cloning vector. A DNA molecule, such as a plasmid, cosmid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

Expression vector. A DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

Recombinant Host. A recombinant host may be any prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, New York (1989).

3. Methods for Introducing an Asn-glycosylation Site in an Antibody Light Chain by Mutating the DNA Sequence Encoding the Protein A. Antibody Structure and Asn-linked Glycosylation Antibody molecules are composed of two identical copies of heavy chains and light chains, which are covalently interconnected by disulfide bonds. For a general discussion, see Schultz et al., "Proteins II: Structure-Function Relationship of Protein Families," in TEXTBOOK OF BIOCHEMISTRY WITH CLINICAL CORRELATIONS, 3rd Ed., T. M. Devlin (ed.), Wiley and Sons, pp. 92–134 (1992); Turner et al., "Antigen Receptor Molecules," in IMMUNOLOGY, 3rd Ed., Roitt et al. (eds.), Mosby, pp. 4.1–4.20 (1993). In the most common type of antibody, IgG, the two heavy chains each have approximately 440 amino acids, while the two light chains each have about 220 amino acids. The carboxyl-terminal one-half of light chains and the carboxyl-terminal three-quarters of heavy chains are highly conserved in amino acid sequence among antibodies with different antigen specificities. These conserved regions in the light and heavy chains are termed "constant regions" and are designated as CL and CH, respectively. The CH regions determine whether a particular antibody belongs to the antibody class IgG, IgA, IgD, IgE, or IgM. The CH regions within a class of antibodies are homologous but differ significantly from the amino acid sequence of the CH regions of other antibody classes.

In contrast, the amino acid sequences of the amino-terminal one-half of the light chains and the amino-terminal of one-quarter of the heavy chains are highly variable among antibodies with different antigen specificities. Particular regions within these variable segments are "hypervariable" and have been designated as "complementarity determining regions" (CDRs) because these regions form the antigen binding site (ABS) that is complementary to the topology of the antigen structure.

Each heavy chain is associated with a light chain such that the amino-terminal ends of both chains are near each other and comprise an antigen binding site. Proteolytic cleavage can be used to fragment an antibody into small, functional units. For example, proteolytic cleavage of an IgG molecule with papain results in the cleavage of the antibody in the hinge peptide of each heavy chain. One product of papain digestion is the carboxyl-terminal one-half of the heavy chains which are bound covalently in a "crystallizable fragment" (Fc). The Fc fragment does not bind antigen. The other cleavage products are identical and consist of an amino-terminal segment of a heavy chain which is associated with an entire light chain. These amino-terminal, or "antigen binding fragments" (Fab) can bind antigen with an affinity similar to that of the intact antibody molecule.

The object of the present invention is to covalently attach a diagnostic or therapeutic principle to an Asn-linked carbohydrate moiety of the light chain variable region of an intact antibody, or antigen-binding fragment thereof. Asn-linked glycosylation, also referred to as "N-linked glycosylation," is a form of glycosylation in which sugar residues are linked through the amide nitrogen of asparagine residues. Intracellular biosynthesis of Asn-linked oligosaccharides occurs in both the lumen of the endoplasmic reticulum and following transport of the protein to the Golgi apparatus. Asn-linked glycosylation occurs at the glycosylation sequence: Asn-X-Thr/Ser, where X may be any amino acid except proline or aspartic acid. Thus, there are 36 possible sequences of three amino acids which code for Asn-linked glycosylation. Considering the degeneracy of the genetic code, there are over a thousand possible nucleotide sequences which encode the glycosylation signal sequences.

B. Mutagenesis

The particular nucleotide sequence which is used to introduce an Asn-linked glycosylation sequence into positions 18–20 will depend upon the naturally-occurring nucleotide sequence. As described below, the introduction of an Asn-linked glycosylation site into the PKAPPA(11)24 protein can be achieved by an alteration of codon 18 from AGG to AAC. Such a mutation of the nucleotide sequence can be accomplished by methods well-known to those in the art.

For example, an Asn-linked glycosylation site can be introduced at positions 18–20 using oligonucleotide-directed mutagenesis and a cloned antibody light chain. In this procedure, a single-stranded DNA template containing the antibody light chain sequence is prepared from a dut⁻ ung⁻ strain of *E. coli* in order to produce a DNA molecule containing a small number of uracil residues in place of thymidine. Such a DNA template can be obtained by M13 cloning or by in vitro transcription using an SP6 promoter. See, for example, Ausubel et al. (eds.), CURRENT PROTOCOLS IN MOLECULAR BIOLOGY, John Wiley and Sons (1987). An oligonucleotide that contains the mutated sequence is synthesized using well-known methods. Id. The oligonucleotide is annealed to the single-stranded template, and T4 DNA polymerase and T4 DNA ligase are used to produce a double-stranded DNA molecule. Transformation of wild-type (dut+ ung+) *E. coli* cells with the double-stranded DNA molecule provides an efficient recovery of mutated DNA.

Detailed protocols for oligonucleotide-directed mutagenesis and related techniques for mutagenesis of cloned DNA are well-known. For example, see Ausubel et al., supra; Sambrook et al., supra.

Alternatively, an Asn-linked glycosylation site can be introduced into an antibody light chain using an oligonucleotide containing the desired mutation as a primer and DNA clones of the variable regions for the antibody light chain, or by using RNA from cells that produce the antibody of interest as a template. Such techniques include, for example, the polymerase chain reaction, as illustrated in Example 1. Also see, Huse, "Combinatorial Antibody Expression Libraries in Filamentous Phage," in ANTIBODY ENGINEERING: A PRACTICAL GUIDE, C. Borrebaeck (ed.), W. H. Freeman and Company, pp. 103-120 (1992). Site-directed mutagenesis can be performed, for example, using the TRANSFORMER™ Site-Directed Mutagenesis Kit (Clontech; Palo Alto, Calif.) according to the manufacturer's instructions.

Alternatively, a glycosylation site can be introduced into an immunoglobulin light chain by synthesizing a light chain gene with mutually priming oligonucleotides in which one of the oligonucleotides contains the desired mutation. Techniques for the construction of large synthetic genes are well known to those in the art. See, for example, Uhlmann, *Gene* 71:29-40 (1988); Wosnick et al., *Gene* 60:115-127 (1988); Ausubel et al., supra.

In summary, an Asn-linked glycosylation site can be introduced at about amino acid position 18 in the light chain of any antibody if two requirements are met. First, the nucleotide sequence surrounding and including the codons for amino acid positions 18-20 of the light chain of the antibody of interest must be available in order to design a complementary oligonucleotide containing the desired mutation. Second, there must be access to either cloned antibody DNA or cells that produce the antibody of interest. Given these two restrictions, the present invention encompasses immunoconjugates comprising murine, humanized, or chimeric antibodies, wherein a diagnostic or therapeutic principle is attached to the antibody component via a carbohydrate moiety located at about amino acid position 18 of the light chain variable region. Such antibodies include intact antibodies and the antigen-binding fragments, Fab, Fab', F(ab)₂, and F(ab')₂.

Moreover, the present invention contemplates the production of immunoconjugates comprising Fv fragments or single chain antibodies. As discussed above, Fv fragments comprise a non-covalent association of heavy and light chain variable regions. In contrast, single-chain antibodies comprise heavy and light polypeptide chains from the variable region of a given antibody which are connected by a peptide linker. See, for example, Bird et al., *Science* 242:423-426 (1988); Ladner et al., U.S. Pat. No. 4,946,778; and Pack et al., *Bio/Technology* 11:1271-1277 (1993).

Generally, Fv fragments and single chain antibodies lack a site for attaching certain diagnostic or therapeutic principles, such as radiometals. However, the introduction of an Asn-linked glycosylation site into a light chain variable region of an Fv fragment or single chain antibody provides a carbohydrate moiety for the attachment of a variety of diagnostic or therapeutic principles, as described below. Although Fv fragments and single chain antibodies are typically produced by prokaryotic host cells, eukaryotic host cells are preferred host cells. In particular, insect cells, yeast cells, and mammalian cells are preferred eukaryotic hosts. Mammalian cells are the most preferred host cells.

Although the present invention provides a method for introducing an Asn-linked glycosylation site at about amino acid position 18-20 of the light chain variable region, it will be understood that the present invention is not so limited. It will occur to those of ordinary skill in the art that it is possible to introduce glycosylation sites at alternative positions of the light chain variable region, or even in the heavy chain variable region. Immunoconjugates of the present invention can be prepared using intact antibodies, antibody fragments, or single chain antibodies which contain a carbohydrate moiety attached at such an alternate glycosylation site as long as the mutated antibodies or fragments retain antigen-binding activity. Suitable alternative glycosylation sites can be identified using molecular modeling techniques that are well-known to those of skill in the art. See, for example, Lesk et al., "Antibody Structure and Structural Predictions Useful in Guiding Antibody Engineering," in ANTIBODY ENGINEERING: A PRACTICAL GUIDE, C. Borrebaeck (ed.), W. H. Freeman and Company, pp. 1-38 (1992); Cheetham, "Engineering Antibody Affinity" Id. at pp. 39-67.

4. Methods for Expressing and Isolating the Protein Product of a Mutated Antibody DNA Sequence A. Methods for Expressing a Mutated Antibody After mutating the nucleotide sequence, mutated DNA is inserted into a cloning vector for further analysis, such as confirmation of the DNA sequence, as illustrated in Example 1. To express the polypeptide encoded by the mutated DNA sequence, the DNA sequence must be operably linked to regulatory sequences controlling transcriptional expression in an expression vector and then, introduced into either a prokaryotic or eukaryotic host cell. In addition to transcriptional regulatory sequences, such as promoters and enhancers, expression vectors include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, and lacZ promoters of *E. coli*, the α-amylase and the $\sigma^{28}$-specific promoters of *B. subtilis*, the promoters of the bacteriophages of Bacillus, Streptomyces promoters, the int promoter of bacteriophage lambda, the bla promoter of the β-lactamase gene of pBR322, and the CAT promoter of the chloramphenicol acetyl transferase gene. Prokaryotic promoters are reviewed by Glick, *J. Ind. Microbiol.* 1:277–282 (1987); Watson et al., MOLECULAR BIOLOGY OF THE GENE, 4th Ed., Benjamin Cummins (1987); Ausubel et al., supra, and Sambrook et al., supra.

An especially preferred prokaryotic host is *E. coli*. Preferred strains of *E. coli* include Y1088, Y1089, CSH18, ER1451, and ER1647 (see, for example, Brown (Ed.), MOLECULAR BIOLOGY LABFAX, Academic Press (1991)). An alternative preferred host is *Bacillus subtilus*, including such strains as BR151, YB886, MI119, MI120, and B170 (see, for example, Hardy, "Bacillus Cloning Methods," in DNA CLONING: A PRACTICAL APPROACH, Glover (Ed.), IRL Press (1985)).

Methods for producing antibody fragments in *E. coli* are well-known to those in the art. See, for example, Huse, "Combinatorial Antibody Expression Libraries in Filamentous Phage," in ANTIBODY ENGINEERING: A PRACTICAL GUIDE, C. Borrebaeck (Ed.), W. H. Freeman and Company, pp. 103–120 (1992); Ward, "Expression and Purification of Antibody Fragments Using *Escherichia coli* as a Host," Id. at pp. 121–138 (1992). Those skilled in the art also know methods for producing in *E. coli* Fv fragments, which consist of variable regions of heavy and light chains. Id. Also, see Whitlow et al., "Single-Chain Fv Proteins and their Fusion Proteins," in NEW TECHNIQUES IN ANTIBODY GENERATION, *Methods* 2(2) (1991).

Moreover, expression systems for cloning antibodies in prokaryotic cells are commercially available. For example, the IMMUNO ZAP ™ Cloning and Expression System (Stratagene Cloning Systems; La Jolla, Calif.) provides vectors for the expression of antibody light and heavy chains in *E. coli*.

Since the expression of a mutated DNA sequence in prokaryotic cells will require subsequent in vitro glycosylation, the present invention preferably encompasses the expression of a mutated DNA sequence in eukaryotic cells, and especially mammalian, insect, and yeast cells. Especially preferred eukaryotic hosts are mammalian cells. Mammalian cells provide post-translational modifications to the cloned polypeptide including proper folding and glycosylation. For example, such mammalian host cells include COS-7 cells (ATCC CRL 1651), non-secreting myeloma cells (SP2/0-AG14; ATCC CRL 1581), Chinese hamster ovary cells (CHO-K1; ATCC CCL 61), rat pituitary cells (GH$_1$; ATCC CCL 82), HeLa S3 cells (ATCC CCL 2.2), and rat hepatoma cells (H-4-II-E; ATCC CRL 1548).

For a mammalian host, the transcriptional and translational regulatory signals may be derived from viral sources, such as adenovirus, bovine papilloma virus, and simian virus. In addition, promoters from mammalian expression products, such as actin, collagen, or myosin, can be employed. Alternatively, a prokaryotic promoter (such as the bacteriophage T3 RNA polymerase promoter) can be employed, wherein the prokaryotic promoter is regulated by a eukaryotic promoter (for example, see Zhou et al., *Mol. Cell. Biol.* 10: 4529–4537 (1990); Kaufman et al., *Nucl. Acids Res.* 19:4485–4490 (1991)). Transcriptional initiation regulatory signals may be selected which allow for repression or activation, so that expression of the genes can be modulated.

In general, eukaryotic regulatory regions will include a promoter region sufficient to direct the initiation of RNA synthesis. Such eukaryotic promoters include the promoter of the mouse metallothionein I gene (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the Rous sarcoma virus promoter (Gorman et al., supra); the cytomegalovirus promoter (Foecking et al., *Gene* 45:101 (1980)); the yeast gal4 gene promoter (Johnston, et al., *Proc. Natl. Acad. Sci.* (USA) 79:6971–6975 (1982); Silver, et al., *Proc. Natl. Acad. Sci.* (USA) 81:5951–5955 (1984)); and the IgG promoter (Orlandi et al., *Proc. Natl. Acad. Sci. USA* 86:3833–3837 (1989)).

Strong regulatory sequences are the most preferred regulatory sequences of the present invention. Examples of such preferred regulatory sequences include the SV40 promoter-enhancer (Gorman, "High Efficiency Gene Transfer into Mammalian cells," in DNA CLONING: A PRACTICAL APPROACH, Volume II, Glover (Ed.), IRL Press pp. 143–190 (1985)), the hCMV-MIE promoter-enhancer (Bebbington et al., *Bio/Technology* 10:169–175 (1992)), and antibody heavy chain promoter (Orlandi et al., *Proc. Natl. Acad. Sci. USA* 86:3833–3837 (1989)). Also preferred are the kappa chain enhancer for the expression of the light chain and the IgH enhancer (Gillies, "Design of Expression Vectors and Mammalian Cell Systems Suitable for Engineered Antibodies," in ANTIBODY ENGINEERING: A PRACTICAL GUIDE, C. Borrebaeck (Ed.), W. H. Freeman and Company, pp. 139–157 (1992); Orlandi et al., supra).

The mutated antibody-encoding sequence and an operably linked promoter may be introduced into eukaryotic cells as a non-replicating DNA molecule, which may either be a linear molecule or, more preferably, a closed covalent circular molecule. Since such molecules are incapable of autonomous replication, the expression of the protein may occur through the transient expression of the introduced sequence. Preferably, permanent expression occurs through the integration of the introduced sequence into the host chromosome.

Preferably, the introduced sequence will be incorporated into a plasmid or viral vector that is capable of autonomous replication in the recipient host. Several possible vector systems are available for this purpose. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired genomic or cDNA sequences into the host chromosome. Additional elements may also be needed for optimal synthesis of mRNA. These elements may include splice signals, as well as transcription promoters, enhancers, and termination signals. The cDNA expression vectors incorporating such elements include those described by Okayama, *Mol. Cell. Biol.* 3:280 (1983), Sambrook et al., supra, Ausubel et al., supra, Bebbington et al., supra, Orlandi et al., supra, and Fouser et al., *Bio/Technology* 10:1121–1127 (1992); Gillies, supra. Genomic DNA expression vectors which include intron sequences are described by Orlandi et al., supra. Also, see generally, Lerner et al. (Eds.), NEW TECHNIQUES IN ANTIBODY GENERATION, *Methods* 2(2) (1991).

In order to obtain mammalian cells that express intact antibody, the expression vector comprising the mutated antibody light chain can be co-transfected into mammalian cells with an antibody heavy chain expression vector. See, for example, Orlandi et al., supra. Alternatively, mammalian cells containing a heavy chain expression vector can be transfected with an expression vector comprising the mutated antibody light chain, and mammalian cells containing an expression vector comprising a mutated light chain can be transfected with a heavy chain expression vector. Moreover, mammalian cells can be transfected with a single expression vector comprising DNA fragments that encode the mutated antibody light chain, as well as DNA fragments that encode antibody heavy chain. See, for example, Gillies, supra; Bebbington et al., supra. Any of these approaches will produce transfected cells that express whole antibody molecules which have the mutated antibody light chain. Standard transfection techniques are well known in the art. See, for example, Sambrook et al., supra; Ausubel et al., supra.

B. Methods for Isolating a Mutated Antibody from Transfected Cells

Transfected cells that carry the expression vector are selected using the appropriate drug. For example, G418 can be used to select transfected cells carrying an expression vector having the aminoglycoside phosphotransferse gene. Southern et al., *J. Mol. Appl. Gen.* 1:327–341 (1982). Alternatively, hygromycin-B can be used to select transfected cells carrying an expression vector having the hygromycin-B-phosphotransferase gene. Palmer et al., *Proc. Natl. Acad. Sci. USA* 84:1055–1059 (1987). Alternatively, aminopterin and mycophenolic acid can be used to select transfected cells carrying an expression vector having the xanthine-guanine phosphoribosyltransferase gene. Mulligan et al., *Proc. Natl. Acad. Sci. USA* 78:2072–2076 (1981).

Transfected cells that produce the mutated antibody can be identified using a variety of methods. For example, any immunodetection assay can be used to identify such "transfectomas." Example 1 provides an illustration of the use of an enzyme-linked immunosorbent assay (ELISA) for such a purpose.

After transfectomas have been identified, the cells are cultured and antibodies are isolated from culture supernatants. Isolation techniques include affinity chromatography with Protein-A Sepharose (for intact antibodies), size-exclusion chromatography, and ion-exchange chromatography. For example, see Coligan et al. (eds.), CURRENT PROTOCOLS IN IMMUNOLOGY, John Wiley and Sons (1991), for detailed protocols.

5. Methods for Preparing Immunoconjugates

A. Preparation of Antibody Fragments

The present invention contemplates the preparation of immunoconjugates from intact mutated antibodies or from antigen-binding antibody fragments. Antibody fragments can be obtained from transfectomas, by proteolytic cleavage of intact mutant antibodies produced by transfectomas, or by proteolytic cleavage of intact antibodies that have naturally-occurring Asn-linked glycosylation sites at position 18–20 of the light chain.

Antibody fragments can be obtained directly from transfectomas by transfecting cells with a heavy chain structural gene that has been mutated. For example, transfectomas should produce Fab fragments if a stop codon was inserted following the sequence of the CH1 domain. Alternatively, transfectomas should produce Fab' or F(ab')$_2$ fragments if a stop codon was inserted after the sequence encoding the hinge region of the heavy chain.

Alternatively, antibody fragments can be prepared from intact antibodies using well-known proteolytic techniques. For example, see, Coligan et al., supra. As an illustration, Example 2 provides a method to obtain Fab fragments using papain. Moreover, F(ab')$_2$ fragments can be obtained using pepsin digestion of intact antibodies. Divalent fragments can be cleaved to monovalent fragments using conventional disulfide bond reducing agents, e.g., cysteine, dithiothreitol (DTT), and the like.

B. Methods of Conjugation

Immunoconjugates can be prepared by indirectly conjugating a diagnostic or therapeutic principle to an intact antibody, or antigen-binding fragment thereof. Such techniques are described in Shih et al., *Int. J. Cancer* 41:832–839 (1988); Shih et al., *Int. J. Cancer* 46:1101–1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, or boron addends, or with detectable labels. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in diagnosis or therapy. Thus, solubilizing functions on the carrier polymer will enhance the serum solubility of the final immunoconjugate. Solubilizing functions also are important for use of immunoconjugates for in vitro immunoassay and in situ detection, as described below. In particular, an aminodextran will be preferred.

The process for preparing an immunoconjugate with an aminodextran carrier typically begins with a dextran polymer, advantageously a dextran of average molecular weight of about 10,000–100,000. The dextran is reacted with an oxidizing agent to effect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to insure substantially complete conversion of the aldehyde functions to Schiff base groups.

A reducing agent, such as $NaBH_4$, $NaBH_3CN$ or the like, is used to effect reductive stabilization of the resultant Schiff base intermediate. The resultant adduct can be purified by passage through a conventional sizing column to remove cross-linked dextrans.

Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, boron addend, or label to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Labels such as enzymes, fluorescent compounds, electron transfer agents, and the like can be linked to a carrier by conventional methods well known to the art. These labeled carriers and the immunoconjugates prepared from them can be used for in vitro immunoassays and for in situ detection, as described below.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier must have at least 50 amino acid residues in the chain, preferably 100–5000 amino acid residues. At least some of the amino acids should be lysine residues or glutamate or aspartate residues. The pendant amines of lysine residues and pendant carboxylates of glutamine and aspartate are convenient for attaching a drug, toxin, chelator, or boron addend. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, boron addend, or label. Alternatively, an intermediate conjugate can be attached to an oxidized antibody component via amine groups that have been introduced in the intermediate conjugate after loading with the diagnostic or therapeutic principle. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a diagnostic or therapeutic principle. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300.

Indirect conjugation to an antibody fragment is illustrated in Example 4.

Alternatively, immunoconjugates can be prepared by directly conjugating an antibody component with a diagnostic or therapeutic principle. The general procedure is analogous to the indirect method of conjugation except that a diagnostic or therapeutic principle is directly attached to an oxidized antibody component. The direct conjugation of chelators to an antibody fragment is illustrated in Example 3.

It will be appreciated that other diagnostic or therapeutic principles can be substituted for the chelators described below. Those of skill in the art will be able to devise conjugation schemes without undue experimentation.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching a diagnostic or therapeutic principle to a carbohydrate moiety and to a free sulfhydryl group. Such a free sulfhydryl group may be located in the hinge region of the antibody component.

6. Use of Immunoconjugates for Diagnosis and Therapy

A. Use of Immunoconjugates for Diagnosis

The method of diagnostic imaging with radiolabeled monoclonal antibodies is well known. See, for example, Srivastava (ed.), RADIOLABELED MONOCLONAL ANTIBODIES FOR IMAGING AND THERAPY, Plenum Press (1988); Chase, "Medical Applications of Radioisotopes," in REMINGTON'S PHARMACEUTICAL SCIENCES, 18th Edition, Gennaro et al. (eds.) Mack Publishing Co., pp. 624–652 (1990); and Brown, "Clinical Use of Monoclonal Antibodies," in BIOTECHNOLOGY AND PHARMACY, Pezzuto et al. (eds.), Chapman andHall, pp. 227–249 (1993). This technique, also known as immunoscintigraphy, uses a gamma camera to detect the location of gamma-emitting radioisotopes conjugated to monoclonal antibodies. Diagnostic imaging can be used to diagnose cardiovascular disease and infectious disease. Brown, supra.

The present invention contemplates the use of immunoconjugates to diagnose cardiovascular disease. For example, immunoconjugates comprising anti-myosin fragments can be used for imaging myocardial necrosis associated with acute myocardial infarction. Immunoconjugates comprising antibody fragments that bind platelets and fibrin can be used for imaging deepvein thrombosis. Moreover, immunoconjugates comprising antibody fragments that bind to activated platelets can be used for imaging atherosclerotic plaque.

Immunoconjugates of the present invention also can be used in the diagnosis of infectious diseases. For example, immunoconjugates comprising antibody fragments that bind specific bacterial antigens can be used to localize abscesses. In addition, immunoconjugates comprising antibody fragments that bind granulocytes and inflammatory leukocytes can be used to localize sites of bacterial infection.

Numerous studies have evaluated the use of monoclonal antibodies for scintigraphic detection of cancer. See, for example, Brown, supra, and references therein. Investigations have covered the major types of solid tumors such as melanoma, colorectal carcinoma, ovarian carcinoma, breast carcinoma, sarcoma, and lung carcinoma. Thus, the present invention contemplates the detection of cancer using immunoconjugates comprising antibody fragments that bind tumor markers to detect cancer. Examples of such tumor markers include carcinoembryonic antigen, alpha-fetoprotein, oncogene products, tumor-associated cell surface antigens, and necrosis-associated intracellular antigens.

In addition to diagnosis, monoclonal antibody imaging can be used to monitor therapeutic responses, detect recurrences of a disease, and guide subsequent clinical decisions.

For diagnostic imaging, radioisotopes may be bound to antibody fragments either directly or indirectly by using an intermediary functional group. Such intermediary functional groups include DTPA and EDTA. The radiation dose delivered to the patient is maintained at as low a level as possible. This is accomplished through the choice of isotope for the best combination of minimum half-life, minimum retention in the body, and minimum quantity of isotope which will permit detection and accurate measurement. Examples of radioisotopes which can be bound to antibodies and are appropriate for diagnostic imaging include $^{99m}$Tc and $^{111}$In.

Studies indicate that antibody fragments, particularly Fab and Fab', provide the best tumor/background ratios. Brown, supra. Thus, Fab and Fab' are preferred antibody fragments for the preparation of immunoconjugates.

The immunoconjugates useful in the invention also can be labeled with paramagnetic ions for purposes of in vivo diagnosis. Elements which are particularly useful for Magnetic Resonance Imaging include Gd, Mn, Dy, and Fe ions.

The present invention also contemplates the use of immunoconjugates to detect the presence of particular antigens in vitro. In such immunoassays, the immunoconjugates may be utilized in liquid phase or bound to a solid-phase carrier. For example, an intact antibody, or antigen-binding fragment thereof, can be attached to a polymer, such as aminodextran, in order to link the antibody component to an insoluble support such as a polymer-coated bead, plate, or tube.

Alternatively, the immunoconjugates of the present invention can be used to detect the presence of particular antigens in tissue sections prepared from a histological specimen. Such in situ detection can be accomplished by applying a detectably-labeled immunoconjugate to the tissue sections. In situ detection can be used to determine the presence of a particular antigen and to determine the distribution of the antigen in the examined tissue. General techniques of in situ detection are well known to those of ordinary skill. See, for example, Ponder, "Cell Marking Techniques and Their Application," in MAMMALIAN DEVELOPMENT: A PRACTICAL APPROACH, Monk (ed.), IRL Press, pp. 115-138 (1987); Coligan et al., supra.

Detectable labels such as enzymes, fluorescent compounds, electron transfer agents, and the like can be linked to a carrier by conventional methods well known to the art. These labeled carriers and the immunoconjugates prepared from them can be used for in vitro immunoassays and for in situ detection, much as an antibody conjugate prepared by direct attachment of the labels to antibody. However, the loading of the immunoconjugates according to the present invention with a plurality of labels can increase the sensitivity of immunoassays or histological procedures, where only a low extent of binding of the antibody, or antibody fragment, to target antigen is achieved.

B. Use of Immunoconjugates for Therapy

Immunoconjugates can be used to treat viral and bacterial infectious diseases, cardiovascular disease, autoimmune disease, and cancer. Brown, supra. The objective of such therapy is to deliver cytotoxic doses of radioactivity, toxin, or drug to target cells, while minimizing exposure to non-target tissues.

As discussed above, a radioisotope can be attached to an intact antibody, or antigen-binding fragment thereof, directly or indirectly, via a chelating agent. For example, $^{67}$Cu, considered one of the more promising radioisotopes for radioimmunotherapy due to its 61.5 hour half-life and abundant supply of beta particles and gamma rays, can be conjugated to an antibody component using the chelating agent, p-bromoacetamidobenzyl-tetraethylaminetetraacetic acid (TETA). Chase, supra. Alternatively, $^{90}$Y, which emits an energetic beta particle, can be coupled to an intact antibody, or antigen-binding fragment thereof, using diethylenetriaminepentaacetic acid (DTPA), as described herein.

Alternatively, boron addends, such as carboranes, can be attached to intact antibodies, or antigen-binding fragments thereof. Carboranes can be prepared with carboxyl functions on pendant side chains, as is well known in the art. Attachment of carboranes to a carrier, such as aminodextran, can be achieved by activation of the carboxyl groups of the carboranes and condensation with amines on the carrier. The intermediate conjugate is then conjugated to the antibody component. After administration of the immunoconjugate, a boron addend is activated by thermal neutron irradiation and converted to radioactive atoms which decay by α-emission to produce highly toxic, short-range effects.

Moreover, immunoconjugates can be prepared in which the therapeutic principle is a toxin or drug. Useful toxins for the preparation of such immunoconjugates include ricin, abrin, pokeweed antiviral protein, gelonin, diphtherin toxin, and Pseudomonas endotoxin. Useful chemotherapeutic drugs for the preparation of immunoconjugates include doxorubicin, daunorubicin, methotrexate, melphalin, chlorambucil, vinca alkaloids, 5-fluorouridine, and mitomycin-C.

C. Administration of Immunoconjugates Generally, the dosage of administered immunoconjugate will vary depending upon such factors as the patient's age, weight, height, sex, general medical condition, and previous medical history. Typically, it is desirable to provide the recipient with a dosage of immunoconjugate which is in the range of from about 1 pg/kg to 10 mg/kg (amount of agent/body weight of patient), although a lower or higher dosage may also be administered. For example, many studies have demonstrated successful diagnostic imaging with doses of 0.1 to 1.0 milligram, while other studies have shown improved localization with doses in excess of 10 milligrams. Brown, supra.

For therapeutic applications, about 10–200 milligrams of immunoconjugate will be administered, normally daily for a period of several days. To reduce patient sensitivity, it may be necessary to reduce the dosage and/or use antibodies from other species and/or use hypoallergenic antibodies, e.g., hybrid human or primate antibodies.

Administration of immunoconjugates to a patient can be intravenous, intraarterial, intraperitoneal, intramuscular, subcutaneous, intrapleural, intrathecal, by perfusion through a regional catheter, or by direct intralesional injection. When administering immunoconjugates by injection, the administration may be by continuous infusion, or by single or multiple boluses.

Immunoconjugates of boron addend-loaded carrier for thermal neutron activation therapy will normally be effected in similar ways. However, it will be advantageous to wait until non-targeted immunoconjugate clears before neutron irradiation is performed. Such clearance can be accelerated by the use of a second antibody, as is known from, e.g., U.S. Pat. No. 4,624,846.

The immunoconjugates of the present invention can be formulated according to known methods to prepare pharmaceutically useful compositions, whereby immunoconjugates are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of immunotherapy, an immunoconjugate and a pharmaceutically acceptable carrier are administered to a patient in a therapeutically effective amount. A combination of an immunoconjugate and a pharmaceutically acceptable carrier is said to be administered in a "therapeutically effective amount" if the amount administered is physiologically significant. An agent is physiologically significant if its presence results in a detectable change in the physiology of a recipient patient.

Additional pharmaceutical methods may be employed to control the duration of action of an immunoconjugate in a therapeutic application. Control release preparations can be prepared through the use of polymers to complex or adsorb an immunoconjugate. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446–1449 (1992). The rate of release of an immunoconjugate from such a matrix depends upon the molecular weight of the immunoconjugate, the amount of immunoconjugate within the matrix, and the size of dispersed particles. Saltzman et al., *Biophysical. J.* 55:163–171 (1989); and Sherwood et al., supra. Other solid dosage forms are described in REMINGTON'S PHARMACEUTICAL SCIENCES, 18th Ed. (1990).

Having now generally described the invention, the same will be more readily understood through reference to the following Examples which are provided by way of illustration, and are not intended to be limiting of the present invention, unless specified.

EXAMPLE 1

Preparation of Immunoconjugates Using Monoclonal Antibodies Which Lack a Naturally-occurring Asn-glycosylation Site in the FR1 Region of the Light Chain Variable Domain (a) Introduction of an Asn-glycosylation Site by Mutagenesis An Asn-glycosylation site is introduced at amino acid position 18 of the FR1 region of the light chain variable domain of a monoclonal antibody by altering the nucleotide sequence which codes for amino acid residues 18–20. As an illustration, the amino acid sequence, $Arg_{18}Val_{19}Ser_{20}$, is found in the framework-1 sequence of the light chain variable region of the murine monoclonal antibody, PKAPPA(11)24, which is produced by MPC-11 cells. Rabbitts et al., *Can. J. Biochem.* 58:176–187 (1980); Kabat et al., SEQUENCES OF PROTEINS OF IMMUNOLOGICAL INTEREST, U.S. Department of Health and Human Services (1983). The Arg residue at position 18 is encoded by the sequence AGG. Id. Therefore, the objective of the mutagenesis technique is to alter the nucleotide sequence from AGG to AAC, which encodes Asn.

The polymerase chain reaction (PCR) technique is used to introduce the Asn-glycoslyation site following the general procedure of Orlandi et al., *Proc. Natl. Acad. Sci. USA* 86:3833–3837 (1989). In this procedure, total cellular RNA is prepared from about $5 \times 10^8$ MPC-11 cells (ATCC CCL 167), and mRNA is selected from total RNA on oligo (dT)-cellulose, using standard procedures. First-strand cDNA synthesis is performed using the VK1FOR primer, which is a VK region 3' primer described by Orlandi et al. A 50 μl reaction mixture containing 10 μg of mRNA, 20 pmol of VK1FOR primer, 250 μM of each dNTP, 10 mM dithiothreitol, 100 mM Tris-HCl (pH 8.3), 10 mM $MgCl_2$, and 140 mM KCl are incubated at 70° C. for 10 minutes and then, cooled. Reverse transcriptase (46 units) is added and the mixture is incubated at 42° C. for one hour. The reaction is terminated by heating the reaction mixture at 90° C. for 5 minutes.

Alternatively, first strand cDNA is synthesized from total cellular RNA from MPC-11 cells using the SUPERSCRIPT ™ preamplification system (Gibco/BRL; Gaithersburg, Md.) with the VK1FOR primer.

The VK sequences are amplified using a 5' primer which encodes the first 20 amino acids of the VK domain, with the exception that amino acids 18–20 encode an Asn-glycosylation site. In this example, amino acid residue at position 18 is encoded by AAC, as discussed above. PCR reaction mixtures contain 10 μl of the first-strand cDNA product, 9 μl of 10× PCR buffer (500 mM KCl, 100 mM Tris-HCl (pH 8.3), 15mM $MgCl_2$, and 0.01% (w/v) gelatin), 5 μl of the VK1FOR and 5' primers, and 5 units of AMPLITAQ ™ DNA polymerase (Perkin Elmer Cetus; Norwalk, Calif.). The mixtures are overlaid with paraffin oil and subjected to 30 rounds of temperature cycling with a programmable heating block. A typical cycle consists of: denaturation at 94° C.

for one minute, annealing at 50° C. for 1.5 minutes, and polymerization at 72° C. for 1.5 minutes.

The DNA sample is extracted twice with ether, once with phenol, once with phenol/chloroform and then, precipitated with ethanol. Alternatively, the DNA sample can be purified following electrophoresis through an agarose gel.

Amplified VK fragments are purified on a 2% agarose gel, using standard techniques. The approximately 300 base pair VK fragments are then digested with the restriction enzymes PvuII and BglII, and ligated into the complementary restriction sites of a cloning vector. Various cloning vectors are commercially available. For example, pGEM ™ vectors (Promega; Madison, Wis.) and ZAP EXPRESS ™ vectors (Stratagene Cloning Systems; La Jolla, Calif.) are useful for cloning the VK fragment. Alternatively, a vector can be used which contains an appropriate immunoglobulin promoter and leader sequence. For example, see Orlandi et al., supra. The ligated DNA is transformed into DH5α competent E. coli cells using a standard calcium chloride method.

To analyze cloned DNA, transformants are grown overnight at 37° C. in SOC (2% Bacto-tryptone, 0.5% Bacto-yeast extract, 10mMNaCl, 2.5 mM KCl, 10 mM $MgCl_2$, 10 mM $MgSO_4$ and 20 mM glucose). The SOC medium contains the appropriate antibiotic to select for the growth of bacteria containing the vectors. For example, the SOC medium contains 50 µg/ml ampicillin to select for the growth of bacteria carrying a pGEM ™ vector. Mini-plasmid DNA preparations of the colonies are prepared using standard techniques and subjected to restriction digest analysis. DNA from positive colonies are sequenced using the dideoxy method of Sanger et al., Proc. Natl. Acad. Sci. USA 75:5463–5467 (1977). The results of DNA sequence determination are used to confirm that no undesirable mutations are introduced by the PCR reaction and that the mutation(s) in the 18–20 region was introduced.

(b) Transfection of Mammalian Cells

Restriction enzymes are used to excise the DNA fragment which contains the VK sequence having an Asn-glycosylation site at position 18 from the staging vector. The DNA fragment is then cloned into an appropriate mammalian expression vector. Such an expression vector should contain the coding sequence of the constant region, an immunoglobulin enhancer, a kappa enhancer and a drug selection marker (e.g., the hygromycin resistance gene). For example, see Orlandi et al., supra.

Approximately 10 µg of the linearized light chain expression vector containing the mutated VK region and 20–30 µg of linearized heavy chain expression vector are co-transfected by electroporation into mammalian cells, using standard techniques. For example, about $10^6$ SP2/0-AG14 non-secreting myeloma cells (ATCC CRL 1581) are transfected using the technique of Co et al., J. Immunol. 148:1149–1154 (1992), or using similar techniques described in either Sambrook et al., supra, or CURRENT PROTOCOLS IN MOLECULAR BIOLOGY, Ausubel et al., eds., John Wiley and Sons (1989). After transfection, cells are grown in 96-well microtiter plates in complete Hybridoma Serum-Free Medium (GIBCO/BRL) at 37° C. in 5% carbon dioxide. Two days later, the selection process is initiated by the addition of medium containing the appropriate selection drug (e.g. hygromycin). Typically, colonies emerge two to three weeks following electroporation. Colonies are transferred to 24-well trays for expansion.

(c) Assay for Antibody-secreting Transfectoma Clones

An ELISA assay is used to select antibody-secreting transfectoma clones. Briefly, supernatants from confluent wells are diluted and 100 µl of each dilution are added in triplicate to ELISA microtiter plates which have been precoated with sheep anti-mouse IgG-specific antibody (The Binding Site Ltd.; San Diego, Calif.). After incubating the microtiter plates for one hour at room temperature, unbound proteins are removed by washing the plates three times with wash buffer (PBS with 0.05% polysorbate-20). Bound antibodies are allowed to react with peroxidase-conjugated goat anti-mouse IgG-specific antibody (HyClone Laboratories; Logan, Utah) After washing the plate three times with wash buffer, 100 µl of substrate solution (3.3 mg/ml of ortho-phenylenediamine and 0.12% hydrogen peroxide in 0.02M citrate buffer (pH 5.0)) are added to each well. Color is allowed to develop in the dark for 30 minutes and the reaction is stopped by the addition of 50 µl of 4M HCl per well. An automated ELISA plate reader (Bio-Tek Instrument; Winooski, Vt.) is used to measure absorbance at 490 nm.

Alternatively, chimeric or humanized mutant antibodies can be detected by coating ELISA microtiter plates with goat anti-human Fab or kappa-specific antibody (Jackson ImmunoResearch; West Grove, Pa.), and detecting bound antibody with peroxidase-conjugated goat anti-human Fc-specific antibody (Jackson ImmunoResearch; West Grove, Pa.).

(d) Antibody Purification and Analysis

Transfectomas are grown as 500 ml cultures in serum-free medium until confluent. Cultures are centrifuged to pellet cells and the supernatants are filtered through a 0.2 micron membrane. Antibodies are isolated by passing supernatants through a three milliliter protein A column by gravity at a rate of 0.5–1 ml/min. The column is then washed with 20 ml of PBS and bound antibodies are eluted with 10 ml of a solution containing 0.1M glycine and 10 mM EDTA (pH 3.5). One milliliter elution fractions are collected in the presence of 10 µl of 3M Tris (pH 8.6). The presence of antibodies is detected by measuring absorbance at 280 nm and eluant fractions exhibiting absorbances above background are pooled, filtered, dialyzed against PBS and concentrated with a Centricon 30 (Amicon; Beverly, Mass.). The final concentrations of antibody are determined by ELISA and antibody concentrations are adjusted to 1 mg/ml in PBS containing 0.01% (w/v) sodium azide.

Light chain glycosylation is confirmed by electrophoresis of the purified antibodies or antibody fragments on a gradient 4–20% SDS-polyacrylamide gel under reducing conditions, using standard techniques. For example, see CURRENT PROTOCOLS IN IMMUNOLOGY, Coligan et al., eds., John Wiley and Sons (1991). The presence of light chain glycosylation is indicated by a higher apparent molecular weight and by the presence of multiple light chain bands.

(e) Preparation of Conjugates

The direct or indirect methods can be used to obtain immunoconjugates, as described below.

EXAMPLE 2

Preparation of Antibody Fragments

Fab, Fab', F(ab)2, or F(ab')2 fragments can be obtained from transfectomas by mutating the heavy chain structural gene in the heavy chain expression vector. Fab expression is accomplished by inserting a stop codon following the sequence of the CH1 domain. In contrast, Fab' or F(ab')2 expression is accomplished by inserting a stop codon after the sequence encoding the hinge region of the heavy chain. Antibody fragments are purified from transfectoma culture supernatants by size exclusion chromatography, ion-exchange chromatography, or affinity chromatography as described in Coligan et al., supra. Alternatively, a commercially-available purification system is used to purify fragments, such as a Quick MAB Column (Sterogen; Santa Clara, Calif.).

Alternatively, antibody fragments can be prepared from intact antibodies by proteolysis. These techniques are well-known to those of skill in the art. For example, see Coligan et al., supra, at pp. 2.8.1–2.8.10. Also see Stanworth et al. "Immunochemical Analysis of Human and Rabbit Immunoglobulins and Their Subunits," in HANDBOOK OF EXPERIMENTAL IMMUNOLOGY, Vol. 1, D. M. Weir, ed., Blackwell Scientific pp 12.1–12.46 (1986) and Parham, "Preparation and Purification of Active Fragments from Mouse Monoclonal Antibodies," Id at pp. 14.1–14.23.

As an example, preactivated papain can be used to prepare F(ab)2 fragments from IgG1 or. Fab fragments from IgG2a and IgG2b, as follows. Papain is activated by incubating 2 mg/ml papain (2× recrystallized suspension, Sigma #P3125) and 0.05M cysteine (free-base, crystalline; Sigma #C7755) for 30 minutes in a 37° C. water bath. To remove cysteine, the papain/cysteine mixture is applied to a PD-10 column (Pharmacia #G-25), which has been equilibrated with 20 ml of acetate/EDTA buffer (0.1M acetate with 3mM EDTA, pH 5.5). Fractions are assayed by measuring absorbance at 280 nm, and the two or three fractions that contain protein are pooled. The concentration of preactivated papain is determined by using the formula: (absorbance at 280 nm)/2.5=mg. preactivated papain/ml.

To prepare antibody for digestion, 10 mg. of antibody in 2 to 5 ml of PBS are dialyzed against acetate/EDTA buffer. Five hundred micrograms of preactivated papain are added to the dialyzed antibody solution, and the mixture is vortexed. After a 6–12 hour incubation in a 37° C. water bath, papain is inactivated by adding crystalline iodoacetamide (Sigma #I6125) to a final concentration of 0.03M. The mixture is then dialyzed against 1 liter of PBS (pH 8.0) at 4° C. for 6–12 hours.

To remove undigested antibody and Fc fragments, the mixture is applied to a protein A-Sepharose column which has been equilibrated in PBS (pH 8.0). Unbound fractions are collected in 2 ml aliquots and pooled. After concentrating the pool to a total volume of 5 ml or less, protein is fractionated by size-exclusion chromatography and the results are analyzed by SDS-PAGE.

EXAMPLE 3

Direct Conjugation at the Carbohydrate Moiety of the FR1 Region of the Light Chain Variable Domain of F(ab')2 Fragments (a) Conjugation of the Murine LL2 F(ab')2 Fragment with Chelator LL2 is a murine monoclonal antibody that has been shown to be effective for the diagnosis and treatment of non-Hodgkins B-cell lymphoma. Goldenberg et al., *J. Clin. Oncol.* 9:548–564 (1991); Murthy et al., *Eur. J. Nucl. Med.* 19:394–401 (1992); The LL2 F(ab')2 fragment was conjugated with either aminobenzyl DTPA (DTPA) or a derivative of DTPA containing the long-chain linker, $-CSNH(CH_2)_{10}NH_2$ (LC-DTPA). Briefly, LL2 F(ab')2 fragment (2.5 mg) in about 1 ml of 50 mM acetate-buffered 0.9% saline (ABS; pH 5.3) was oxidized in the dark by treatment with sodium metaperiodate (210 µl of a 5.68 mg/ml solution) at 0° C. for one hour. The reaction mixture was treated with ethylene glycol (20 µl) to decompose the unreacted periodate and the oxidized antibody fragment was purified using a Sephadex G-50/80 column (Pharmacia; Piscataway, N.J.) equilibrated in PBS (pH 6.1). The oxidized fragment was then reacted with excess DTPA or LC-DTPA. After 40 hours at room temperature, the Schiff base was reduced by $NaBH_3CN$. Conjugated antibody was purified using a centrifuged size-exclusion column (Sephadex G-50/80) equilibrated in 0.1M acetate (pH 6.5). The concentrations of antibody conjugates were determined by measuring absorbance at 280 nm.

The ratio of chelator molecules per molecule of antibody fragment was determined by a metal-binding assay. The assay was performed by mixing an aliquot of LL2 F(ab')2-chelator conjugate with 0.1M ammonium acetate (pH 7) and 2M triethanolamine, and incubating the mixture at room temperature with a known excess of cobalt acetate spiked with $^{57}$cobalt acetate. After 30 minutes, EDTA (pH 7) was added to a final concentration of 10 mM. After a further 10 minute incubation, the mixture was analyzed by instant thin layer chromatography (ITLC) using 10mMEDTA for development. The fraction of radioactivity bound to antibody was determined by counting sections of ITLC strips on a gamma counter. The results indicated that there were about 6 molecules of DTPA per antibody fragment and about 5 molecules of LC-DTPA per antibody fragment.

(b) Determination of the Immunoreactivity of LL2 F(ab')2-chelator Conjugates

The immunoreactivities of the LL2 F(ab')2-DTPA and LL2 F(ab')2-LC-DTPA conjugates were determined using an ELISA assay. The results demonstrated that LL2 F(ab')2 and the DTPA and LC-DTPA conjugates exhibited similar binding activity toward an LL2 anti-idiotype antibody.

In addition, the immunoreactivities of the LL2 F(ab')2-DTPA and LL2 F(ab')2-LC-DTPA conjugates were examined in a binding competition assay. In these experiments, a human chimeric LL2 (IgG/kappa) was used to compete with LL2 F(ab')2 or its conjugates for binding to Raji lymphoma cells (ATCC CCL 86). Raji cells were cultured in DMEM medium, supplemented with 10% fetal calf serum and 2mML-glutamine. Cells were maintained at 37° C. in 5% carbon dioxide. Cell medium and components were obtained from Gibco/BRL (Gathersburg, Md.).

In these studies, 1 µg of the chimeric LL2 (IgG/kappa) was incubated with $5 \times 10^5$ Raji cells in the presence of various concentrations of LL2 F(ab')2 or its conjugates in a final volume of 100 µl of PBS supplemented with 1% fetal calf serum and 0.01% (w/v) sodium azide (PBS-FA). The mixtures were incubated for 30 minutes at 4° C., and then washed three times with PBS to remove unbound antibodies. The extent of residual binding by chimeric LL2 after competition was determined by adding 100 μl of a solution containing a goat anti-human Fc-specific antibody labeled with fluorescein isothiocyanate (20× diluted stock solution in PBS-FA), and incubating for 30 min at 4° C. After washing the mixture three times with PBS, fluorescence intensity was measured using a FACSCAN fluorescence activated cell sorter. The results of these studies demonstrated that LL2 F(ab')$_2$ and its conjugates exhibited similar binding to Raji cells.

Thus, these studies demonstrate that both conjugates were immunoreactive and exhibited binding activities comparable to unconjugated LL2 F(ab')$_2$ fragments.

(c) Labeling with $^{111}$Indium

The LL2 F(ab')$_2$-chelator conjugates were labeled with $^{111}$Indium as follows. $^{111}$Indium chloride was buffered at pH 5.5 using ammonium acetate such that the final acetate concentration was about 0.2M. $^{111}$Indium acetate was added to a solution of LL2 F(ab')$_2$-conjugate in 0.1M acetate (pH 6.5), and the mixture was incubated for about one hour. Reaction mixtures contained either 9.7 μg of LL2 F(ab')$_2$-DTPA and 72.6 μCi of $^{111}$Indium, or 10 μg of LL2 F(ab')$_2$-LC-DTPA and 126.7 μCi of $^{111}$Indium.

The extent of $^{111}$indium incorporation was analyzed by incubating the labeling mixture with 10 mM EDTA for ten minutes, followed by ITLC examination using 10 mM EDTA for development. In this assay, unbound $^{111}$indium moves to the solution front, while antibody-bound $^{111}$indium remains at the origin. The presence of any colloidal $^{111}$indium was assayed by ITLC (co-spotted with human serum albumin) using a water:ethanol::ammonia (5:2:1) solution for development. In this system, the fraction of radioactivity at the origin represents colloidal $^{111}$indium. In addition, all labeling mixtures were analyzed using radio-high pressure liquid chromatography (radio-HPLC).

The results of these studies indicated that $^{111}$indium-labeled LL2 F(ab')$_2$-DTPA had a specific activity of 7.47 μCi/μg protein, and that $^{111}$indium was incorporated by 97.4%, as determined by ITLC, or 92.5%, as determined by radio-HPLC. Moreover, $^{111}$indium-labeled LL2 F(ab')$_2$-LC-DTPA had a specific activity of 12.67 μCi/μg protein, and $^{111}$indium was incorporated by 95.6%, as determined by ITLC, or 94%, as determined by radio-HPLC. The amount of colloidal $^{111}$indium is typically about 1 to 3%.

(d) Labeling with $^{90}$Yttrium

LL2 F(ab')$_2$-chelator conjugates were prepared as described above. The conjugates were labeled with $^{90}$yttrium, as follows. Briefly, commercially available $^{90}$yttrium chloride (DuPont NEN; 17.68 μl; 5.63 mCi) was buffered with 35.4 μl of 0.5M acetate (pH 6.0). The solution was allowed to stand for 5–10 minutes at room temperature, and then used for radiolabeling.

$^{90}$Yttrium-labeled LL2 F(ab')$_2$-DTPA was prepared by mixing $^{90}$yttrium acetate (128.7 μCi) with LL2 F(ab')$_2$-DTPA (30 μg; 8.3 μl), incubating at room temperature for one hour, and diluting with 90 μl of 0.1M acetate (pH 6.5). $^{90}$Yttrium-labeled LL2 F(ab')$_2$-LC-DTPA was prepared by mixing $^{90}$yttrium acetate (109.5 μCi) with LL2 F(ab')$_2$-LC-DTPA (30 μg; 7.6 μl), incubating at room temperature for one hour, and diluting with 90 μl of 0.1M acetate (pH 6.5). The result of the labeling procedure was tested by ITLC in two solvent systems, and by HPLC, as described above.

$^{90}$Yttrium-labeled LL2 F(ab')$_2$-DTPA had a specific activity of 4.29 μCi/μg protein, while $^{90}$yttrium-labeled LL2 F(ab')$_2$-LC-DTPA had a specific activity of 3.65 μCi/μg protein. Radio-HPLC analysis indicated that $^{90}$yttrium was incorporated in LL2 F(ab')$_2$-DTPA by 96%, while $^{90}$yttrium was incorporated in LL2 F(ab')$_2$-LC-DTPA by 90%.

EXAMPLE 4

Indirect Conjugation at the Carbohydrate Moiety of the FR1 Region of the Light Chain Variable Domain of F(ab')$_2$ Fragments (a) Preparation of the Intermediate Conjugate The murine LL2 F(ab')$_2$ fragment was conjugated with doxorubicin via dextran, using the method of Shih et al., *Int. J. Cancer* 41:832–839 (1988). Briefly, amino dextran was prepared by dissolving one gram of dextran (m.w. 18 kD; Sigma Chemical Co.; St. Louis, Mo.) in 70 ml of water. The dextran was partially oxidized to form polyaldehyde dextran by adding 0.5 gram of sodium metaperiodate, and stirring the solution at room temperature overnight. After concentrating the mixture with an Amicon cell (YM10 membrane; MWCO=10,000), the polyaldehyde dextran was purified by Sephadex G-25 chromatography and lyophilized to give about 900 grams of white powder. Polyaldehyde dextran was then treated with two equivalents of 1,3-diamino-2-hydroxypropane in aqueous phase for 24 hours at room temperature. The resultant Schiff base was stabilized by addition of sodium borohydride (0.311 mmol per 2.15 mmol of 1,3-diamino-2-hydroxypropane) to the mixture. The mixture was allowed to incubate at room temperature for six hours. Amino dextran was purified using a Sephadex G-25 column.

Doxorubicin (Sigma Chemical Co.; St. Louis, Mo.) was activated by adding one milliliter of anhydrous DMF to 0.1 mmole of doxorubicin in a dried Reacti-vial, followed by a solution of N-hydroxysuccinimide (23 mg, 0.2 mmole; Sigma) in 750 μl of anhydrous DMF and a solution of 1,3-dicyclohexylcarbodiimide (41.5 mg, 0.2 mmol; Sigma) in 750 μl of anhydrous DMF. The reaction mixture was stirred in the dark at room temperature for 16 hours under anhydrous conditions. The side product, i.e., the urea derivative, did not precipitate well in this solvent system. The precipitate was centrifuged and the solution was stored in a sealed bottle at −20° C.

Doxorubicin-dextran intermediate conjugate was prepared by dissolving aminodextran (18 kD; 10 mg) in two milliliters of PBS (pH 7.2) and gradually adding 0.7 ml of the above N-hydroxy-succinimide-activated doxorubicin solution. Thus, 50 moles of doxorubicin were present per mole of aminodextran. The solution was stirred at room temperature for five hours and after removing any precipitate, the conjugate was purified using a Sephadex G-25 column. Doxorubicin-dextran conjugate was characterized by a doxorubicin/dextran ratio of 14.

Alternatively, doxorubicin-dextran conjugate was prepared by reacting doxorubicin with 1-ethyl-3(3-dimethylaminopropyl)carbodiimide, as described by Shih et al., *Int. J. Cancer* 41:832–839 (1988). Also, see Shih et al., *Cancer Research* 51:4192–4198 (1991).

EXAMPLE 5

Introduction of an Asn-linked Glycosylation Site in the VK FR1 Region of Humanized MN14

An Asn-glycosylation site was introduced into the VK FR1 region of humanized MN14, which is an antibody that binds carcinoembryonic antigen. Briefly, the nucleotide sequence encoding $Arg_{18}$ was mutated to a nucleotide sequence encoding $Asn_{18}$ using the PCR method described in Example 1. In this case, DNA from the light chain expression vector for humanized MN14 was used as a template for PCR. The VKFOR1 primer of Orlandi et al. was used as the 3' primer. The 5' primer consisted of a 57-mer encoding the first 20 amino acids of the MN14 VK domain, with the exception that the codon at position 18 encoded Asn. The approximately 300 base pair PCR product was digested with PvuII and BglII, and ligated into complementary sites in a staging or cloning vector. DH5α competent cells were transformed with the staging or cloning vector using a standard calcium chloride method. For example, see, Ausubel et al., supra.

The DNA fragment containing the humanized MN14 VK sequence with an Asn-glycosylation site at amino acid position 18 was subcloned into a pSVhyg-based light chain expression vector. SP2/0-AG14 non-secreting myeloma cells were co-transfected by electroporation with the linearized light chain expression vector and with a linearized heavy chain expression vector. Transfectomas were selected using hygromycin-B and cultured to produce antibody.

Antibody was purified and analyzed on an SDS-PAGE reducing gel. The light chain of the glycosylated humanized MN14 migrated as multiple bands and ran at a higher molecular weight, compared to non-glycosylated MN14 light chain. This result indicates that the new Asn-linked glycosylation site was used for carbohydrate addition.

Significantly, the MN14 blocking activities of the glycosylated MN14 antibody and the non-glycosylated MN14 antibody were found to be substantially the same. Thus, glycosylation at the VK FR1 region of humanized MN14 does not affect immunoreactivity.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

(b) Site-specific Attachment of the Intermediate Conjugate to LL2 F(ab')$_2$

LL2 F(ab')$_2$ fragment (25 mg) in 5 ml of PBS (pH 5.5) was oxidized in the dark by treatment with sodium metaperiodate (800 μl of a 21.5 mg/ml solution) at room temperature for 60 minutes. The reaction mixture was treated with ethylene glycol (50 μl) to decompose the unreacted periodate and the oxidized antibody fragment was purified using a Sephadex G-25 column equilibrated in 0.05M HEPES (pH 7.4). The oxidized fragment was then concentrated to 5 mg/ml in 0.05M HEPES (pH 7.4) and reacted with the doxorubicin-dextran conjugate (22 mg). After 24 hours at room temperature, the Schiff base was reduced by $NaBH_3CN$. Conjugated antibody was purified using a Sepharose CL-6B column.

Using this procedure, an average of about nine doxorubicin molecules can be coupled to each LL2 F(ab')$_2$ fragment at the carbohydrate site of the FR1 region of the light chain variable domain. This ratio was determined by measuring the concentration of doxorubicin ($A_{482}$) and protein ($A_{280}$). The conjugate retains 80% of the immunoactivity of the unconjugated LL2 F(ab')$_2$ fragment, as determined by the flow cytometry method described above.

What is claimed is:

1. A soluble immunoconjugate, comprising:
   (a) a glycosylated antibody fragment selected from the group consisting of Fab, Fab', F(ab)$_2$, F(ab')$_2$, Fv and single chain Fv, which comprises a light chain variable region having a carbohydrate moiety attached at about amino acid position 18 of said light chain variable region; and
   (b) a loaded carrier, comprising a polymer carrier having at least one free amine group and a plurality of drug, toxin, chelator, boron addend or detectable label molecules covalently bound to said polymer carrier,
wherein said loaded carrier is covalently bound through said at least one free amine group of said polymer carrier to said carbohydrate moiety of said antibody fragment,
and wherein said immunoconjugate retains the immunoreactivity of said antibody fragment.

2. The soluble immunoconjugate of claim 1, wherein said antibody fragment is a mutated antibody fragment having a non-natural Asn-glycosylation site at about amino acid position 18 of the light chain of said antibody fragment.

3. The soluble immunoconjugate of claim 1, wherein said polymer carrier is an aminodextran or a polypeptide of at least 50 amino acids in length.

4. A soluble immunoconjugate, comprising:
   (a) a glycosylated antibody fragment selected from the group consisting of Fab, Fab', F(ab)$_2$, F(ab')$_2$, Fv, and single chain Fv, which comprises a light chain variable region having a carbohydrate moiety attached at about amino acid position 18 of said light chain variable region; and
   (b) at least one non-antibody moiety selected from the group consisting of a drug, a toxin, a chelator, a boron addend and a detectable label molecule,
wherein each said non-antibody moiety is covalently bound to said carbohydrate moiety of said antibody fragment,
and wherein said immunoconjugate retains the immunoreactivity of said antibody fragment.

5. The soluble immunoconjugate of claim 4, wherein said antibody fragment is a mutated antibody fragment comprising a non-natural Asn-glycosylation site at about amino acid position 18 of the light chain of said antibody fragment.

6. A method for diagnosing the presence of a disease in a mammal, said method comprising the steps of:
   (a) administering to a mammal an effective imaging amount of a composition comprising an immunoconjugate and a pharmaceutically acceptable carrier, wherein said immunoconjugate comprises a detectable label and an antibody fragment having a carbohydrate moiety attached at about amino acid position 18 of the light chain of said antibody fragment, wherein said detectable label is conjugated to said carbohydrate moiety of said antibody fragment, and wherein said antibody fragment specifically binds to an antigen which is associated with said disease; and (b) using in vivo imaging to detect the presence of said immunoconjugate at disease sites.

7. The method of claim 6, wherein said detectable label is a radioisotope or a paramagnetic ion.

8. The method of claim 7, wherein said antibody fragment is LL2-F(ab')$_2$, and wherein said radioisotope is $^{111}$Indium.

9. A mutated recombinant antibody or antibody fragment having a non-natural Asn-glycosylation site at about position 18 of the light chain of said antibody or antibody fragment.

10. An antibody fragment according to claim 9, wherein said fragment is selected from the group consisting of Fab, Fab', F(ab)$_2$, F(ab')$_2$, Fv, and single chain Fv.

11. A method for preparing a glycosylated mutated recombinant antibody or antibody fragment, comprising the steps of:

(a) culturing transformed host cells which express and glycosylate a mutated antibody or antibody fragment comprising a mutated light chain and a heavy chain, said host cells being transformed with an expression vector into which is cloned a mutated DNA molecule encoding a mutated light chain containing a non-natural Asn-glycosylation site at about amino acid position 18; and (b) recovering expressed and glycosylated mutated antibody or antibody fragment from said cultured host cells.

12. A method for treating a disease in a mammal, said method comprising administering to said mammal an effective therapeutic amount of a composition comprising an immunoconjugate and a pharmaceutically acceptable carrier, wherein said immunoconjugate comprises an antibody fragment having a carbohydrate moiety attached at about amino acid position 18 of the light chain of said antibody fragment and a non-antibody moiety selected from the group consisting of a drug, a toxin, a chelator, a boron addend and a therapeutic radioisotope, wherein said non-antibody moiety is covalently bound to said carbohydrate moiety of said antibody fragment, and wherein said antibody fragment specifically binds to an antigen which is associated with said disease.

13. The method of claim 12, wherein said antibody fragment is LL2-F(ab')$_2$, and wherein said radioisotope is $^{90}$Yttrium.

14. The method of claim 12, wherein said antibody fragment is LL2-F(ab')$_2$, and wherein said drug is doxorubicin.

15. A method for preparing an immunoconjugate, comprising covalently binding a loaded carrier to the carbohydrate moiety of an antibody fragment, wherein said antibody fragment is selected from the group consisting of Fab, Fab', F(ab)$_2$, F(ab')$_2$, Fv, and single chain Fv, wherein said antibody fragment contains a carbohydrate moiety in the light chain of said antibody fragment at about amino acid position 18, wherein said loaded carrier comprises a polymer carrier having at least one free amine group and a plurality of drug, toxin, chelator, boron addend or detectable label molecules covalently bound to the polymer carrier, wherein said loaded carrier is covalently bound through said at least one free amine group of said polymer carrier to said carbohydrate moiety of said antibody fragment, and wherein said immunoconjugate retains the immunoreactivity of said antibody fragment.

16. The method of claim 15, wherein said loaded carrier is an aminodextran or a polypeptide of at least fifty amino acids in length.

17. A method for preparing an immunoconjugate, comprising covalently binding a non-antibody moiety to the carbohydrate moiety of an antibody fragment, wherein said antibody fragment is selected from the group consisting of Fab, Fab' F(ab) F(ab')$_2$, Fv, and single chain Fv, wherein said antibody fragment contains a carbohydrate moiety in the light chain of said antibody fragment at about amino acid position 18, wherein said non-antibody moiety is selected from the group consisting of a drug, a toxin, a chelator, a boron addend and a detectable label molecule, and wherein said immunoconjugate retains the immunoreactivity of said antibody fragment.

* * * * *